United States Patent [19]
Beckmann et al.

[11] Patent Number: 5,972,675
[45] Date of Patent: Oct. 26, 1999

[54] PROTEIN KINASE WHICH SPECIFICALLY PHOSPHORYLATES BRCA-1

[75] Inventors: Richard P. Beckmann, Indianapolis; Teresa F. Burke, Fishers; Kimberly S. Cocke, New Palestine; Stephanie J. Lemke, Indianapolis, all of Ind.

[73] Assignee: Eli Lilly and Company, Indianapolis, Ind.

[21] Appl. No.: 08/785,464

[22] Filed: Jan. 17, 1997

Related U.S. Application Data
[60] Provisional application No. 60/010,781, Jan. 29, 1996.

[30] Foreign Application Priority Data

Feb. 15, 1996 [DE] Germany ................................ 9603149

[51] Int. Cl.⁶ ..................................................... C12N 9/12
[52] U.S. Cl. ............................................................. 435/194
[58] Field of Search .............................................. 435/194

[56] References Cited

PUBLICATIONS

Miki et al. (1994) Science, 266, "A Strong Candidate for the Breast and Ovarian Cancer Susceptibility Gene BRCA–1", pp. 66–71.
Thomas et al. (1997) Cell Growth Differ., 8(7), "Induction of Phosphorylation on BRCA–1 During the Cell Cycle and after DNA Damage", pp. 801–809.
Chen et al. (1995) Science, 270, "Aberrant Subcellular Localization of BRCA1 in Breast Cancer", pp. 789–791.
Chen et al. (1996) Cancer Res., 56(14), "BRCA1 is a 220–kDA Nuclear Phosphoprotein That is Expressed and Phosphorylated in a Cell Cycle–Dependent Manner", pp. 3168–3172.
Jensen et al. (1996) Nature Gen., 12(3), "BRCA1 is Secreted and Exhibits Properties of a Granin", pp. 303–308.
Wang et al. (1997) Oncogene, 15(2), "BRCA1 Proteins are Transported to the Nucleus in the Absence of Serum and Splice Variants BRCA1a, BRCA1b are Tyrosine Phosphoproteins that Associate with E2F, Cyclins and Cyclin Dependent Kinases", pp. 143–157.
Wilson et al. (1996) Nature Gen., 13(3), "BRCA1 Protein Products: Antibody Specificity . . . ", pp. 264–265.
Koonin et al. (1996) Nature Gen., 13(3), ". . . Functional Motifs . . . ", pp. 266–268.
Diamandis (1996) Nature Gen., 13(3), ". . . and Secreted Tumor Suppressors", pp. 268.
Bradley et al. 1996) Nature Gen., 13(3), ". . . and Secreted Tumor Suppressors", pp. 268–269.
Jensen et al. (1996) Nature Gen., 13(3), ". . . and Secreted Tumor Suppressors", pp. 269–272.

*Primary Examiner*—Jon P. Weber
*Attorney, Agent, or Firm*—Paul J. Gaylo; David E. Boone

[57] ABSTRACT

The present invention describes a protein kinase which catalyzes the in phosphorylation of BRCA-1 protein. The present invention also describes the use of the BRCA-1 protein kinase as a molecular target for therapeutic intervention and/or as a therapeutic tool for diagnosing and treating breast and/or ovarian cancer.

7 Claims, No Drawings

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 301 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:1:

Asn Asp Arg Arg Thr Pro Ser Thr Glu Lys Lys Val Asp Leu Asn Ala
1               5                   10                  15

Asp Pro Leu Cys Glu Arg Lys Glu Trp Asn Lys Gln Lys Leu Pro Cys
            20                  25                  30

Ser Glu Asn Pro Arg Asp Thr Glu Asp Val Pro Trp Ile Thr Leu Asn
        35                  40                  45

Ser Ser Ile Gln Lys Val Asn Glu Trp Phe Ser Arg Ser Asp Glu Leu
    50                  55                  60

Leu Gly Ser Asp Asp Ser His Asp Gly Glu Ser Glu Ser Asn Ala Lys
65                  70                  75                  80

Val Ala Asp Val Leu Asp Val Leu Asn Glu Val Asp Glu Tyr Ser Gly
                85                  90                  95

Ser Ser Glu Lys Ile Asp Leu Leu Ala Ser Asp Pro His Glu Ala Leu
            100                 105                 110

Ile Cys Lys Ser Glu Arg Val His Ser Lys Ser Val Glu Ser Asn Ile
        115                 120                 125

Glu Asp Lys Ile Phe Gly Lys Thr Tyr Arg Lys Lys Ala Ser Leu Pro
    130                 135                 140

Asn Leu Ser His Val Thr Glu Asn Leu Ile Ile Gly Ala Phe Val Thr
145                 150                 155                 160

Glu Pro Gln Ile Ile Gln Glu Arg Pro Leu Thr Asn Lys Leu Lys Arg
                165                 170                 175

Lys Arg Arg Pro Thr Ser Gly Leu His Pro Glu Asp Phe Ile Lys Lys
            180                 185                 190

```
    Ala Asp Leu Ala Val Gln Lys Thr Pro Glu Met Ile Asn Gln Gly Thr
                195                 200                 205

Asn Gln Thr Glu Gln Asn Gly Gln Val Met Asn Ile Thr Asn Ser Gly
                210                 215                 220

His Glu Asn Lys Thr Lys Gly Asp Ser Ile Gln Asn Glu Lys Asn Pro
    225                 230                 235                 240

Asn Pro Ile Glu Ser Leu Glu Lys Glu Ser Ala Phe Lys Thr Lys Ala
                    245                 250                 255

Glu Pro Ile Ser Ser Ser Ile Ser Asn Met Glu Leu Glu Leu Asn Ile
                    260                 265                 270

His Asn Ser Lys Ala Pro Lys Lys Asn Arg Leu Arg Arg Lys Ser Ser
                275                 280                 285

Thr Arg His Ile His Ala Leu Glu Leu Val Val Ser Arg
                290                 295                 300
```

(2) INFORMATION FOR SEQ ID NO:2:

(i) SEQUENCE CHARACTERISTICS:
        (A) LENGTH: 106 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Asn Asp Arg Arg Thr Pro Ser Thr Glu Lys Lys Val Asp Leu Asn Ala
1               5                   10                  15

Asp Pro Leu Cys Glu Arg Lys Glu Trp Asn Lys Gln Lys Leu Pro Cys
                20                  25                  30

Ser Glu Asn Pro Arg Asp Thr Glu Asp Val Pro Trp Ile Thr Leu Asn
            35                  40                  45

Ser Ser Ile Gln Lys Val Asn Glu Trp Phe Ser Arg Ser Asp Glu Leu
        50                  55                  60

Leu Gly Ser Asp Asp Ser His Asp Gly Glu Ser Glu Ser Asn Ala Lys
65                  70                  75                  80

Val Ala Asp Val Leu Asp Val Leu Asn Glu Val Asp Glu Tyr Ser Gly
                85                  90                  95

Ser Ser Glu Lys Ile Asp Leu Leu Ala Ser
                100                 105
```

(2) INFORMATION FOR SEQ ID NO:3:

(i) SEQUENCE CHARACTERISTICS:
        (A) LENGTH: 196 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

```
Asn Asp Arg Arg Thr Pro Ser Thr Glu Lys Lys Val Asp Leu Asn Ala
1               5                   10                  15

Asp Pro Leu Cys Glu Arg Lys Glu Trp Asn Lys Gln Lys Leu Pro Cys
                20                  25                  30

Ser Glu Asn Pro Arg Asp Thr Glu Asp Val Pro Trp Ile Thr Leu Asn
            35                  40                  45

Ser Ser Ile Gln Lys Val Asn Glu Trp Phe Ser Arg Ser Asp Glu Leu
        50                  55                  60
```

```
Leu Gly Ser Asp Asp Ser His Asp Gly Glu Ser Glu Ser Asn Ala Lys
 65                  70                  75                  80

Val Ala Asp Val Leu Asp Val Leu Asn Glu Val Asp Glu Tyr Ser Gly
                 85                  90                  95

Ser Ser Glu Lys Ile Asp Leu Leu Ala Ser Asp Pro His Glu Ala Leu
            100                 105                 110

Ile Cys Lys Ser Glu Arg Val His Ser Lys Ser Val Glu Ser Asn Ile
            115                 120                 125

Glu Asp Lys Ile Phe Gly Lys Thr Tyr Arg Lys Lys Ala Ser Leu Pro
        130                 135                 140

Asn Leu Ser His Val Thr Glu Asn Leu Ile Ile Gly Ala Phe Val Thr
145                 150                 155                 160

Glu Pro Gln Ile Ile Gln Glu Arg Pro Leu Thr Asn Lys Leu Lys Arg
                165                 170                 175

Lys Arg Arg Pro Thr Ser Gly Leu His Pro Glu Asp Phe Ile Lys Lys
            180                 185                 190

Ala Asp Leu Ala
        195
```

(2) INFORMATION FOR SEQ ID NO:4:

(i) SEQUENCE CHARACTERISTICS:
        (A) LENGTH: 92 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Asn Asp Arg Arg Thr Pro Ser Thr Glu Lys Lys Val Asp Leu Asn Ala
 1               5                  10                  15

Asp Pro Leu Cys Glu Arg Lys Glu Trp Asn Lys Gln Lys Leu Pro Cys
                 20                  25                  30

Ser Glu Asn Pro Arg Asp Thr Glu Asp Val Pro Trp Ile Thr Leu Asn
            35                  40                  45

Ser Ser Ile Gln Lys Val Asn Glu Trp Phe Ser Arg Ser Asp Glu Leu
        50                  55                  60

Leu Gly Ser Asp Asp Ser His Asp Gly Glu Ser Glu Ser Asn Ala Lys
 65                  70                  75                  80

Val Ala Asp Val Leu Asp Val Leu Asn Glu Val Asp
                 85                  90
```

(2) INFORMATION FOR SEQ ID NO:5:

(i) SEQUENCE CHARACTERISTICS:
        (A) LENGTH: 309 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:5:

```
Glu Glu Arg Gly Thr Gly Leu Glu Glu Asn Asn Gln Glu Glu Gln Ser
 1               5                  10                  15

Met Asp Ser Asn Leu Gly Glu Ala Ala Ser Gly Cys Glu Ser Glu Thr
                 20                  25                  30

Ser Val Ser Glu Asp Cys Ser Gly Leu Ser Ser Gln Ser Asp Ile Leu
            35                  40                  45
```

```
Thr Thr Gln Gln Arg Asp Thr Met Gln His Asn Leu Ile Lys Leu Gln
     50              55                  60
Gln Glu Met Ala Glu Leu Glu Ala Val Leu Glu Gln His Gly Ser Gln
 65              70                  75                      80
Pro Ser Asn Ser Tyr Pro Ser Ile Ile Ser Asp Ser Ser Ala Leu Glu
                 85                  90                  95
Asp Leu Arg Asn Pro Glu Gln Ser Thr Ser Glu Lys Ala Val Leu Thr
             100                 105                 110
Ser Gln Lys Ser Ser Glu Tyr Pro Ile Ser Gln Asn Pro Glu Gly Leu
         115                 120                 125
Ser Ala Asp Lys Phe Glu Val Ser Ala Asp Ser Ser Thr Ser Lys Asn
     130                 135                 140
Lys Glu Pro Gly Val Glu Arg Ser Ser Pro Ser Lys Cys Pro Ser Leu
145             150                 155                     160
Asp Asp Arg Trp Tyr Met His Ser Cys Ser Gly Ser Leu Gln Asn Arg
                165                 170                 175
Asn Tyr Pro Ser Gln Glu Glu Leu Ile Lys Val Val Asp Val Glu Glu
             180                 185                 190
Gln Gln Leu Glu Glu Ser Gly Pro His Asp Leu Thr Glu Thr Ser Tyr
         195                 200                 205
Leu Pro Arg Gln Asp Leu Glu Gly Thr Pro Tyr Leu Glu Ser Gly Ile
     210                 215                 220
Ser Leu Phe Ser Asp Asp Pro Glu Ser Asp Pro Ser Glu Asp Arg Ala
225             230                 235                     240
Pro Glu Ser Ala Arg Val Gly Asn Ile Pro Ser Ser Thr Ser Ala Leu
                245                 250                 255
Lys Val Pro Gln Leu Lys Val Ala Glu Ser Ala Gln Ser Pro Ala Ala
             260                 265                 270
Ala His Thr Thr Asp Thr Ala Gly Tyr Asn Ala Met Glu Glu Ser Val
         275                 280                 285
Ser Arg Glu Lys Pro Glu Leu Thr Ala Ser Thr Glu Arg Val Asn Lys
     290                 295                 300
Arg Met Ser Met Val
305
```

PROTEIN KINASE WHICH SPECIFICALLY PHOSPHORYLATES BRCA-1

This application claims benefit of provisional Application No. 60/010,781 filed Jan. 29, 1996.

FIELD OF THE INVENTION

The present invention relates generally to a BRCA-1 protein kinase and its manipulation for the control of cellular processes. The present invention also relates to the use of the BRCA-1 protein kinase as a molecular target for therapeutic intervention and/or as a therapeutic tool for diagnosing and treating breast and/or ovarian cancer.

BACKGROUND OF THE INVENTION

An estimated 182,000 new cases of invasive breast cancer occurred in the United States during 1995 and over 46,000 deaths resulted from this disease. The search for and identification of specific genetic elements which contribute to the development of breast cancer is an essential part of achieving better treatment and earlier diagnosis.

The discovery of BRCA-1 is a recent example of a burgeoning effort in molecular biology which is focused on the identification of specific disease-associated genes. BRCA-1 is the first gene discovered in an intensive worldwide search for genes associated with enhanced susceptibility to breast and ovarian cancer.

The BRCA-1 gene consists of 100 Kb of DNA which comprises 22 coding exons and encodes a protein of 1863 amino acids. (Gene Bank Accession No. U14680). Sequence analysis has provided little insight into BRCA-1 function since only a short region within the amino terminus (comprising less than 10% of the coding sequence) shows significant homology to known protein sequences. Specifically, this region consists of a putative zinc finger domain which may be critical in facilitating interactions between BRCA-1 and other proteins. Although the role this gene plays in breast cancer development is unknown, it is clear that germline mutations within this gene are associated with an 87% and 44% lifetime risk for breast cancer and ovarian cancer, respectively.

Studies suggest that mutations in BRCA-1 may play a role in nearly half the cases of familial breast cancer. However, there is little evidence indicating that this gene is involved in spontaneous (non-hereditary) breast cancer.

The present invention is the result of an effort to identify protein kinases which functionally interact with BRCA-1 in order to gain insight into BRCA-1's functional activity in regulatory pathways or other physiological processes of the cell.

Protein kinases are known to mediate cellular signals important for growth and differentiation. Typically, increased expression is associated with alterations in normal cellular processes. Some of these affected cellular processes include cell proliferation, differentiation and cancer, including, for example, breast cancer and ovarian cancer.

The identification and characterization of one or more novel protein kinases should provide important insights into the mechanisms underlying oncogenesis and cellular growth control pathways. Such kinases may also be an important target for the development of chemotherapeutic agents.

There thus exists a need to identify protein kinases associated with BRCA-1 and to manipulate these protein kinases in order to diagnose or treat pathological conditions and control cellular processes. The present invention satisfies this need and provides a variety of related advantages as well.

SUMMARY OF THE INVENTION

The present invention is directed to protein kinases, or functional fragments thereof which interact with and phosphorylate specific amino acid residues within the BRCA-1 protein. The present invention also is directed to a method of diagnosing and/or treating cancer, more particularly, breast and/or ovarian cancer utilizing these protein kinases.

DEFINITIONS

The terms and abbreviations used in this document have their normal meanings unless otherwise designated. For example "°C." refers to degrees Celsius; "N" refers to normal or normality; "mmol" refers to millimole or millimoles; "g" refers to gram or grams; "ml" means milliliter or milliliters; "M" refers to molar or molarity; "$\mu$g" refers to microgram or micrograms; and "$\mu$l" refers to microliter or microliters.

All nucleic acid sequences, unless otherwise designated, are written in the direction from the 5' end to the 3' end, frequently referred to as "5' to 3'".

All amino acid or protein sequences, unless otherwise designated, are written commencing with the amino terminus ("N-terminus") and concluding with the carboxy terminus ("C-terminus"). "Base pair" or "bp" as used herein refers to DNA or RNA. The abbreviations A,C,G, and T correspond to the 5'-monophosphate forms of the deoxyribonucleosides (deoxy)adenosine, (deoxy)cytidine, (deoxy)guanosine, and (deoxy)thymidine, respectively, when they occur in DNA molecules. The abbreviations U,C,G, and A correspond to the 5'-monophosphate forms of the ribonucleosides urodine, cytidine, guanosine, and adenosine, respectively when they occur in RNA molecules. In double stranded DNA, base pair may refer to a pairing of A with T or C with G. In a DNA/RNA, heteroduplex base pair may refer to a pairing of A with U or C with G. (See the definition of "complementary", infra.)

The terms "cleavage" or "restriction" of DNA refers to the catalytic cleavage of the DNA with a restriction enzyme that acts only at certain sequences in the DNA ("sequence-specific endonucleases"). The various restriction enzymes used herein are commercially available and their reaction conditions, cofactors, and other requirements were used as would be known to one of ordinary skill in the art. Appropriate buffers and substrate amounts for particular restriction enzymes are specified by the manufacturer or can be readily found in the literature.

"Ligation" refers to the process of forming phosphodiester bonds between two nucleic acid fragments (T. Maniatis, et al., supra., p. 146). Unless otherwise provided, ligation may be accomplished using known buffers and conditions with a DNA ligase, such as T4 DNA ligase.

The term "plasmid" refers to an extrachromosomal (usually) self-replicating genetic element. Plasmids are generally designated by a lower case "p" followed by letters and/or numbers. The starting plasmids herein are either commercially available, publicly available on an unrestricted basis, or can be constructed from available plasmids in accordance with published procedures. In addition, equivalent plasmids to those described are known in the art and will be apparent to the ordinarily skilled artisan.

The term "reading frame" means the nucleotide sequence from which translation occurs "read" in triplets by the translational apparatus of transfer RNA (tRNA) and ribosomes and associated factors, each triplet corresponding to a particular amino acid. A frameshift mutation occurs when a base pair is inserted or deleted from a DNA segment. When this occurs, the result is a different protein from that coded for by the DNA segment prior to the frameshift mutation. To insure against this, the triplet codons corresponding to the desired polypeptide must be aligned in multiples of three from the initiation codon, i.e. the correct "reading frame" being maintained.

"Recombinant DNA cloning vector" as used herein refers to any autonomously replicating agent, including, but not limited to, plasmids and phages, comprising a DNA molecule to which one or more additional DNA segments can or have been added.

The term "recombinant DNA expression vector" as used herein refers to any recombinant DNA cloning vector in which a promoter and other regulatory elements to control transcription of the inserted DNA.

The term "expression vector system" as used herein refers to a recombinant DNA expression vector in combination with one or more trans-acting factors that specifically influence transcription, stability, or replication of the recombinant DNA expression vector. The trans-acting factor may be expressed from a co-transfected plasmid, virus, or other extrachromosomal element, or may be expressed from a gene integrated within the chromosome.

"Transcription" as used herein refers to the process whereby information contained in a nucleotide sequence of DNA is transferred to a complementary RNA sequence.

The term "transfection" as used herein refers to the taking up of an expression vector by a host cell whether or not any coding sequences are in fact expressed. Numerous methods of transfection are known to the ordinarily skilled artisan, for example, calcium phosphate co-precipitation, and electroporation. Successful transfection is generally recognized when any indication of the operation of this vector occurs within the host cell.

The term "transformation" as used herein means the introduction of DNA into an organism so that the DNA is replicable, either as an extrachromosomal element or by chromosomal integration. Methods of transforming bacterial and eukaryotic hosts are well known in the art, many of which methods are summarized in J. Sambrook, et al., "Molecular Cloning: A Laboratory Manual" (1989).

The term "translation" as used herein refers to the process whereby the genetic information of messenger RNA is used to specify and direct the synthesis of a polypeptide chain.

The term "vector" as used herein refers to a nucleic acid compound used for the transformation of cells with polynucleotide sequences corresponding to appropriate protein molecules which when combined with appropriate control sequences confer specific properties on the host cell to be transformed. Plasmids, viruses, and bacteriophage are suitable vectors. Artificial vectors are constructed by joining DNA molecules from different sources. The term "vector" as used herein includes Recombinant DNA cloning vectors and Recombinant DNA expression vectors.

The terms "complementary" or "complementarity" as used herein refers to the pairing of bases, purines and pyrimidines, that associate through hydrogen bonding in double stranded nucleic acid. The following base pairs are complementary: guanine and cytosine; adenine and thymine; and adenine and uracil.

The term "hybridization" as used herein refers to a process in which a strand of nucleic acid joins with a complementary strand through base pairing. The conditions employed in the hybridization of two non-identical, but very similar, complementary nucleic acids varies with the degree of complementarity of the two strands and the length of the strands. Such techniques and conditions are well known to practitioners in this field.

"Isolated amino acid sequence" refers to any amino acid sequence, however constructed or synthesized, which is locationally distinct from the naturally occurring sequence.

"Isolated DNA compound" refers to any DNA sequence, however constructed or synthesized, which is locationally distinct from its natural location in genomic DNA.

"Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation.

The term "promoter" refers to a DNA sequence which directs transcription of DNA to RNA.

A "probe" as used herein is a nucleic acid compound or a fragment thereof which hybridizes with a nucleic acid compound which encodes either the entire sequence SEQ ID NO:2, a sequence complementary to SEQ ID NO:2, or a part thereof.

The term "PCR" as used herein refers to the widely-known polymerase chain reaction employing a thermally-stable polymerase.

DETAILED DESCRIPTION OF THE INVENTION

The present invention relates to the identification and characterization of a BRCA-1 protein kinase which regulates a variety of cellular processes with regard to the BRCA-1 gene. By identifying this protein kinase, the control of different cellular processes regarding breast and/or ovarian cancer is contemplated. More specifically, this protein kinase provides a molecular target for therapeutic intervention in the form of using the protein kinase as a reagent in an assay for screening BRCA-1 phosphorylation or in an assay to screen compounds for their ability to inhibit/prevent or promote BRCA-1 phosphorylation. The use of BRCA-1 protein kinase in gene therapy is also contemplated.

As used herein, the term "BRCA-1 protein kinase" or "BRCA-1 related protein kinase" refers to specific protein kinase(s) which interact with and phosphorylates specific amino acid residues (as further defined hereinafter) within the BRCA-1 protein. Additional factors and/or proteins associated with the protein kinase of the present invention which alter its activity toward BRCA-1, are intended to also be encompassed within the scope of the present invention.

The BRCA-1 protein kinase of the present invention was first identified as a protein which co-purified with BRCA-1 when the protein fragments were expressed and purified from insect cells. The BRCA-1 protein kinase of the present invention is characterized as requiring either $Mg^{++}$ or $Mn^{++}$ for activity but is independent of $Ca^{++}$. The kinase activity is unstable in insect cell lysates treated with 0.1% SDS but is stable in lysates containing urea at concentrations at 3M or less. The kinase appears to reside in the cytoplasm since it can be solubilized from cells in the absence of detergents. Lysates prepared from insect cells have active kinase in isotonic buffers containing 0.5% NP-40 (a non-ionic detergent) and in hypotonic buffers containing no detergent.

Preliminary data indicates that the kinase binds Sepharose SP resin (a cation ion exchange resin) at pH's below about 8 and a low ionic strength thereby indicating that the protein kinase has a pI (isoelectric point) between about pH 5 and about pH 8.

The above physical properties provide skilled artisans with the information necessary to isolate the BRCA-1 protein kinase of the present invention. Identification of the BRCA-1 protein kinase can be readily confirmed by examining the phosphorylation patterns of BRCA-1 protein as disclosed herein.

Because of distinct patterns of phosphorylation demonstrated in specific amino acid residues of the BRCA-1 protein, aberrations in the normal cellular processes associated with the BRCA-1 gene, such as those leading to uncontrolled malignant cell growth, can be detected utilizing the present invention.

It is understood that limited modifications may be made without destroying biological functions of the BRCA-1 protein kinase and that only a portion of the entire primary structure may be required in order to effect a particular activity. Such biological functions and activities can include, for example, signal transduction, ligand binding and/or kinase activity. Minor modifications of these sequences which do not destroy their activity also fall within the definition of BRCA-1 related protein kinase and within the definition of the protein claimed as such.

Moreover, fragments of the BRCA-1 protein kinase, which retain the function of the entire protein as well as functional domains that contain at least one function of the intact protein are included within the definition. Functional domains can include, for example, active ligand binding and catalytic domains. The boundaries of such domains are not important as long as activity is maintained. It is also understood that minor modifications of the primary amino acid sequence can result in proteins which have substantially equivalent or enhanced function. These modifications may be deliberate, as through site-directed mutagenesis, or may be accidental such as through mutation in hosts which produce such kinases. All of these modifications are included as long as biological function is retained. Further, as noted above, additional factors and/or proteins can play a role with regard to the activity of the present invention. Various molecules can be attached to the protein kinase of the present invention. For example, other proteins, carbohydrates, lipids or phosphate groups can be attached to the protein kinase of the present invention. Such modifications are intended to be encompassed within the present invention.

The term "substantially purified" when used to describe the state of the kinase denotes the protein free of a portion of the other proteins and molecules normally associated with or occurring with such kinases in their native environment. Such substantially purified kinases can be derived from natural sources, recombinantly expressed or synthesized by in vitro methods so long as some portion of normally associated molecules are absent.

The present invention provides a BRCA-1 protein kinase or functional fragment thereof. The present invention also provides a substantially purified BRCA-1 related protein kinase, or functional fragment thereof.

The kinase activity demonstrated in the present invention showed that a BRCA-1 fragment from exon 11 (produced in Sf9 insect cells and partially purified over glutathione agarose) could be phosphorylated when it was incubated in the presence of $\gamma^{32}P$-ATP. The amino acid sequence which corresponds to the region of BRCA-1 where phosphorylation mediated by BRCA-1 protein kinase has been demonstrated is set forth below:

```
Asn Asp Arg Arg Thr Pro Ser Thr Glu Lys Lys Val Asp Leu Asn Ala
 1               5                  10                  15

Asp Pro Leu Cys Glu Arg Lys Glu Trp Asn Lys Gln Lys Leu Pro Cys
                 20                  25                  30

Ser Glu Asn Pro Arg Asp Thr Glu Asp Val Pro Trp Ile Thr Leu Asn
             35                  40                  45

Ser Ser Ile Gln Lys Val Asn Glu Trp Phe Ser Arg Ser Asp Glu Leu
         50                  55                  60

Leu Gly Ser Asp Asp Ser His Asp Gly Glu Ser Glu Ser Asn Ala Lys
 65                  70                  75                  80

Val Ala Asp Val Leu Asp Val Leu Asn Glu Val Asp Glu Tyr Ser Gly
                 85                  90                  95

Ser Ser Glu Lys Ile Asp Leu Leu Ala Ser Asp Pro His Glu Ala Leu
                100                 105                 110

Ile Cys Lys Ser Glu Arg Val His Ser Lys Ser Val Glu Ser Asn Ile
             115                 120                 125

Glu Asp Lys Ile Phe Gly Lys Thr Tyr Arg Lys Lys Ala Ser Leu Pro
        130                 135                 140

Asn Leu Ser His Val Thr Glu Asn Leu Ile Ile Gly Ala Phe Val Thr
145                 150                 155                 160

Glu Pro Gln Ile Ile Gln Glu Arg Pro Leu Thr Asn Lys Leu Lys Arg
                165                 170                 175

Lys Arg Arg Pro Thr Ser Gly Leu His Pro Glu Asp Phe Ile Lys Lys
            180                 185                 190

Ala Asp Leu Ala Val Gln Lys Thr Pro Glu Met Ile Asn Gln Gly Thr
            195                 200                 205

Asn Gln Thr Glu Gln Asn Gly Gln Val Met Asn Ile Thr Asn Ser Gly
        210                 215                 220

His Glu Asn Lys Thr Lys Gly Asp Ser Ile Gln Asn Glu Lys Asn Pro
225                 230                 235                 240

Asn Pro Ile Glu Ser Leu Glu Lys Glu Ser Ala Phe Lys Thr Lys Ala
                245                 250                 255

Glu Pro Ile Ser Ser Ser Ile Ser Asn Met Glu Leu Glu Leu Asn Ile
            260                 265                 270

His Asn Ser Lys Ala Pro Lys Lys Asn Arg Leu Arg Arg Lys Ser Ser
        275                 280                 285

Thr Arg His Ile His Ala Leu Glu Leu Val Val Ser Arg
        290                 295                 300
``` which is hereinafter referred to as SEQ ID NO:1.

Other amino acid sequences which correspond to the region of BRCA-1 where phosphorylation mediated by BRCA-1 protein kinase has been demonstrated are set forth below as:

```
Asn Asp Arg Arg Thr Pro Ser Thr Glu Lys Lys Val Asp Leu Asn Ala
 1               5                  10                  15

Asp Pro Leu Cys Glu Arg Lys Glu Trp Asn Lys Gln Lys Leu Pro Cys
                 20                  25                  30

Ser Glu Asn Pro Arg Asp Thr Glu Asp Val Pro Trp Ile Thr Leu Asn
             35                  40                  45

Ser Ser Ile Gln Lys Val Asn Glu Trp Phe Ser Arg Ser Asp Glu Leu
         50                  55                  60
```

```
Leu Gly Ser Asp Asp Ser His Asp Gly Glu Ser Glu Ser Asn Ala Lys
65                  70                  75                  80

Val Ala Asp Val Leu Asp Val Leu Asn Glu Val Asp Glu Tyr Ser Gly
                85                  90                  95

Ser Ser Glu Lys Ile Asp Leu Leu Ala Ser Asp
            100                 105
``` which is hereinafter referred to as SEQ ID NO:2 or as:

```
Asn Asp Arg Arg Thr Pro Ser Thr Glu Lys Lys Val Asp Leu Asn Ala
1               5                   10                  15

Asp Pro Leu Cys Glu Arg Lys Glu Trp Asn Lys Gln Lys Leu Pro Cys
            20                  25                  30

Ser Glu Asn Pro Arg Asp Thr Glu Asp Val Pro Trp Ile Thr Leu Asn
        35                  40                  45

Ser Ser Ile Gln Lys Val Asn Glu Trp Phe Ser Arg Ser Asp Glu Leu
    50                  55                  60

Leu Gly Ser Asp Asp Ser His Asp Gly Glu Ser Glu Ser Asn Ala Lys
65                  70                  75                  80

Val Ala Asp Val Leu Asp Val Leu Asn Glu Val Asp Glu Tyr Ser Gly
                85                  90                  95

Ser Ser Glu Lys Ile Asp Leu Leu Ala Ser Asp Pro His Glu Ala Leu
            100                 105                 110

Ile Cys Lys Ser Glu Arg Val His Ser Lys Ser Val Glu Ser Asn Ile
        115                 120                 125

Glu Asp Lys Ile Phe Gly Lys Thr Tyr Arg Lys Lys Ala Ser Leu Pro
        130                 135                 140

Asn Leu Ser His Val Thr Glu Asn Leu Ile Ile Gly Ala Phe Val Thr
145                 150                 155                 160

Glu Pro Gln Ile Ile Gln Glu Arg Pro Leu Thr Asn Lys Leu Lys Arg
                165                 170                 175

Lys Arg Arg Pro Thr Ser Gly Leu His Pro Glu Asp Phe Ile Lys Lys
            180                 185                 190

Ala Asp Leu Ala Val
            195
``` which is hereinafter referred to as SEQ ID NO:3.

Another amino acid sequence that corresponds to the region of BRCA-1 where phosphorylation mediated by BRCA-1 protein kinase has been demonstrated is set forth below:

```
Asn Asp Arg Arg Thr Pro Ser Thr Glu Lys Lys Val Asp Leu Asn Ala
1               5                   10                  15

Asp Pro Leu Cys Glu Arg Lys Glu Trp Asn Lys Gln Lys Leu Pro Cys
            20                  25                  30

Ser Glu Asn Pro Arg Asp Thr Glu Asp Val Pro Trp Ile Thr Leu Asn
        35                  40                  45

Ser Ser Ile Gln Lys Val Asn Glu Trp Phe Ser Arg Ser Asp Glu Leu
    50                  55                  60

Leu Gly Ser Asp Asp Ser His Asp Gly Glu Ser Glu Ser Asn Ala Lys
65                  70                  75                  80

Val Ala Asp Val Leu Asp Val Leu Asn Glu Val Asp Glu
                85                  90
``` which is hereinafter referred to as SEQ ID NO:4.

Still other another amino acid sequence tha tcorresponds to the region of BRCA-1 where phosphorylation mediated by BRCA-1 protein kinase has been demostrated is set forth below:

---

| Ile | Gln | Lys | Val | Asn | Glu | Trp | Phe | Ser | Arg | Ser | Asp | Glu | Leu | Leu | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Ser | Asp | Asp | Ser | His | Asp | Gly | Glu | Ser | Glu | Ser | Asn | Ala | Lys |
|-----|-----|-----|-----|-----|-----|-----|-----|-----|-----|-----|-----|-----|-----|
|     |     |     | 20  |     |     |     |     | 25  |     |     |     |     | 30  |

--- which is hereinafter referred to as SEQ ID NO:5.

Yet another amino acid sequence that corresponds to the region of BRCA-1 where phosphorylation mediated by BRCA-1 protein kinase has been demonstrated is set forth below:

---

Glu Glu Arg Gly Thr Gly Leu Glu Glu Asn Asn Gln Glu Gln Ser
 1           5               10              15

Met Asp Ser Asn Leu Gly Glu Ala Ala Ser Gly Cys Glu Ser Glu Thr
             20              25              30

Ser Val Ser Glu Asp Cys Ser Gly Leu Ser Ser Gln Ser Asp Ile Leu
         35              40              45

Thr Thr Gln Gln Arg Asp Thr Met Gln His Asn Leu Ile Lys Leu Gln
     50              55              60

Gln Glu Met Ala Glu Leu Glu Ala Val Leu Glu Gln His Gly Ser Gln
65              70              75              80

Pro Ser Asn Ser Tyr Pro Ser Ile Ile Ser Asp Ser Ser Ala Leu Glu
             85              90              95

Asp Leu Arg Asn Pro Glu Gln Ser Thr Ser Glu Lys Ala Val Leu Thr
             100             105             110

Ser Gln Lys Ser Ser Glu Tyr Pro Ile Ser Gln Asn Pro Glu Gly Leu
         115             120             125

Ser Ala Asp Lys Phe Glu Val Ser Ala Asp Ser Ser Thr Ser Lys Asn
     130             135             140

Lys Glu Pro Gly Val Glu Arg Ser Ser Pro Ser Lys Cys Pro Ser Leu
145             150             155             160

Asp Asp Arg Trp Tyr Met His Ser Cys Ser Gly Ser Leu Gln Asn Arg
             165             170             175

Asn Thr Pro Ser Gln Glu Glu Leu Ile Lys Val Val Asp Val Glu Glu
             180             185             190

Gln Gln Leu Glu Glu Ser Gly Pro His Asp Leu Thr Glu Thr Ser Tyr
         195             200             205

Leu Pro Arg Gln Asp Leu Glu Gly Thr Pro Tyr Leu Glu Ser Gly Ile
210             215             220

Ser Leu Phe Ser Asp Asp Pro Giu Ser Asp Pro Ser Glu Asp Arg Ala
225             230             235             240

Pro Glu Ser Ala Arg Val Gly Asn Ile Pro Ser Ser Thr Ser Ala Leu
             245             250             255

Lys Val Pro Gln Leu Lys Val Ala Glu Ser Ala Gln Ser Pro Ala Ala
             260             265             270

Ala His Thr Thr Asp Thr Ala Gly Tyr Asn Ala Met Glu Glu Ser Val
             275             280             285

Ser Arg Glu Lys Pro Glu Leu Thr Ala Ser Thr Glu Arg Val Asn Lys
     290             295             300

-continued

Arg Met Ser Met Val
305 which is hereinafter referred to as SEQ ID NO:6.

Skilled artisans will recognize that both the kinase and substrate proteins of the present invention can be synthesized by a number of different methods. All of the amino acid compounds of the invention can be made by chemical methods well known in the art, including solid phase peptide synthesis, or recombinant methods. Both methods are described in U.S. Pat. No. 4,617,149, incorporated herein by reference.

The principles of solid phase chemical synthesis of polypeptides are well known in the art and may be found in general texts in the area. See, e.g., H. Dugas and C. Penney, BIOORGANIC CHEMISTRY, (1981) Springer-Verlag, New York, pgs. 54–92. For examples, peptides may be synthesized by solid-phase methodology utilizing an Applied Biosystems 430A peptide synthesizer (commercially available from Applied Biosystems, Foster City Calif.) and synthesis cycles supplied by Applied Biosystems. Protected amino acids, such as t-butoxycarbonyl-protected amino acids, and other reagents are commercially available from many chemical supply houses.

Sequential t-butoxycarbonyl chemistry using double couple protocols are applied to the starting p-methyl benzhydryl amine resins for the production of C-terminal carboxamides. For the production of C-terminal acids, the corresponding pyridine-2-aldoxime methiodide resin is used. Asparagine, glutamine, and arginine are coupled using preformed hydroxy benzotriazole esters. The following side chain protection may be used:

Arg, Tosyl

Asp, cyclohexyl

Glu, cyclohexyl

Ser, Benzyl

Thr, Benzyl

Tyr, 4-bromo carbobenzoxy

Removal of the t-butoxycarbonyl moiety (deprotection) may be accomplished with trifluoroacetic acid (TFA) in methylene chloride. Following completion of the synthesis, the peptides may be deprotected and cleaved from the resin with anhydrous hydrogen fluoride containing 10% metacresol. Cleavage of the side chain protecting group(s) and of the peptide from the resin is carried out at zero degrees centigrade or below, preferably −20° C. for thirty minutes followed by thirty minutes at 0° C.

After removal of the hydrogen fluoride, the peptide/resin is washed with ether, and the peptide extracted with glacial acetic acid and then lyophilized. Purification is accomplished by sizesexclusion chromatography on a Sephadex G-10 (Pharmacia Biotech, Inc., Piscataway, N.J.) column in 10% acetic acid.

The proteins (kinase and substrate) of the present invention may also be produced by recombinant methods. Recombinant methods are preferred if a high yield is desired. A general method for the construction of any desired DNA sequence is provided in J. Brown, et al., Methods in Enzymology, 68:109 (1979). See also, J. Sambrook, et al., supra.

The basic steps in the recombinant production of desired proteins are:

a) construction of a synthetic or semi-synthetic DNA encoding the protein of interest;

b) integrating said DNA into an expression vector in a manner suitable for the expression of the protein of interest, either alone or as a fusion protein;

c) transforming an appropriate eukaryotic or prokaryotic host cell with said expression vector, d) culturing said transformed or transfected host cell in a manner to express the protein of interest; and e) recovering and purifying the recombinantly produced protein of interest.

In general, prokaryotes can be used for cloning of DNA sequences in constructing the vectors of this invention. Prokaryotes may also be employed in the production of the protein of interest. For example, the *Escherichia coli* K12 strain 294 (ATCC No. 31446) is particularly useful for the prokaryotic expression of foreign proteins. A commercialy available *E. coli* strain which is preferred for prokaryotic expression of the fusion proteins of the invention is designated DH10B. DH10B is available from Gibco BRL, P.O. Box 68, Grand Island, N.Y. 14072-0068. Other strains of *E. coli* which may be used (and their relevant genotypes) include the following.

| Strain | Genotype |
|--------|----------|
| DH5a | F$^-$ (j80dlacZDM15), D(lacZYA-argF)U169 supE44, 1$^-$, hsdR17($r_K^-$, $m_K^+$), recA1, endA1, gyrA96, thi-1, relA1 |
| HB101 | supE44, hsdS20($r_B^-$ $m_B^-$), recA13, ara-14, proA2 lacY1, galK2, rpsL20, xyl-5, mtl-1, mcrB, mrr |
| JM109 | recA1, e14$^-$(mcrA), supE44, endA1, hsdR17($r_K^-$, $m_K^+$), gyrA96, relA1, thi-1, Δ(lac-proAB), F'[traD36, proAB+ lacI$^q$, lacZΔM15] |
| RR1 | supE44, hsdS20($r_B^-$ $m_B^-$), ara-14 proA2, lacY1, galK2, rpsL20, xyl-5, mtl-5 |
| c1776 | F$^-$, ton, A53, dapD8, minA1, supE42(glnV42), D(gal-uvrB)40, minB2, rfb-2, gyrA25, thyA142, oms-2, metC65, oms-1, D(bioH-asd)29, cycB2, cycA1, hsdR2, 1$^-$ |
| 294 | endA, thi$^-$, hsr$^-$, hsm$_k^+$ (U. S. Pat. 4,366,246) |
| LE392 | F$^-$, hsdR514(r$^-$m$^-$), supE44, supF58, lacY1, or Dlac(I–Y)6, galK2, glaT22, metBq, trpR55, 1$^-$ |

These strains are all commercially available from suppliers such as: Bethesda Research Laboratories, Gaithersburg, Md. 20877 and Stratagene Cloning Systems, La Jolla, Calif. 92037; or are readily available to the public from sources such as the American Type Culture Collection, 12301 Parklawn Drive, Rockville, Md., 10852-1776.

Except where otherwise noted, these bacterial strains can be used interchangeably. The genotypes listed are illustrative of many of the desired characteristics for choosing a bacterial host and are not meant to limit the invention in any way. The genotype designations are in accordance with standard nomenclature. See, for example, J. Sambrook, et al., supra. A preferred strain of *E. coli* employed in the cloning and expression of the genes of this invention is RV308, which is available from the ATCC under accession number ATCC 31608, and is described in U.S Pat. No. 4,551,433, issued Nov. 5, 1985. While they are still preferred when substantial amounts of fusion protein are desired, the facile nature of numerous eukaryotic expression systems results in a preference for these systems when modest amounts of the biologically active fusion proteins are desired.

In addition to the strains of *E. coli* discussed supra, bacilli such as *Bacillus subtilis*, other enterobacteriaceae such as *Salmonella typhimurium* or *Serratia marcescans*, and various Pseudomonas species may also be used. In addition to these gram-negative bacteria, other bacteria, especially Streptomyces, spp., may be employed in the prokaryotic cloning and expression of the proteins of this invention.

Promoters suitable for use with prokaryotic hosts include the b-lactamase [vector pGX2907 (ATCC 39344) contains the replicon and b-lactamase gene] and lactose promoter systems [Chang et al., *Nature* (London), 275:615 (1978); and Goeddel et al., *Nature* (London), 281:544 (1979)], alkaline phosphatase, the tryptophan (trp) promoter system [vector pATH1 (ATCC 37695) is designed to facilitate expression of an open reading frame as a trpE fusion protein under control of the trp promoter] and hybrid promoters such as the tac promoter (isolatable from plasmid pDR540 ATCC-37282). However, other functional bacterial promoters, whose nucleotide sequences are generally known, enable one of skill in the art to ligate them to DNA encoding the proteins of the instant invention using linkers or adapters to supply any required restriction sites. Promoters for use in bacterial systems also will contain a Shine-Dalgarno sequence operably linked to the DNA encoding the desired polypeptides. These examples are illustrative rather than limiting.

The proteins of this invention may be synthesized either by direct expression or as a fusion protein comprising the protein of interest as a translational fusion with another protein or peptide which may be removable by enzymatic or chemical cleavage. It is often observed in the production of certain peptides in recombinant systems that expression as a fusion protein prolongs the lifespan, increases the yield of the desired peptide, or provides a convenient means of purifying the protein of interest. A variety of peptidases (e.g. trypsin) which cleave a polypeptide at specific sites or digest the peptides from the amino or carboxy termini (e.g. diaminopeptidase) of the peptide chain are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See e.g., P. Carter, "Site Specific Proteolysis of Fusion Proteins", Chapter 13 in PROTEIN PURIFICATION: FROM MOLECULAR MECHANISMS TO LARGE SCALE PROCESSES, American Chemical Society, Washington, D.C. (1990).

In addition to cloning and expressing the genes of interest in the prokaryotic systems discussed above, the proteins of the present invention may also be produced in eukaryotic systems. The present invention is not limited to use in a particular eukaryotic host cell. A variety of eukaryotic host cells are available from depositories such as the American Type Culture Collection (ATCC) and are suitable for use with the vectors of the present invention. The choice of a particular host cell depends to some extent on the particular expression vector used to drive expression of the protein-encoding nucleic acids of the present invention. Exemplary host cells suitable for use in the present invention are listed in Table I.

TABLE I

| Host Cell | Origin | Source |
|---|---|---|
| HepG-2 | Human Liver Hepatoblastoma | ATCC HB 8065 |
| CV-1 | African Green Monkey Kidney | ATCC CCL 70 |
| LLC-MK$_2$ | Rhesus Monkey Kidney | ATCC CCL 7 |
| 3T3 | Mouse Embryo Fibroblasts | ATCC CCL 92 |
| CHO-K1 | Chinese Hamster Ovary | ATCC CCL 61 |
| HeLa | Human Cervix Epitheloid | ATCC CCL 2 |
| RPMI8226 | Human Myeloma | ATCC CCL 155 |
| H4IIEC3 | Rat Hepatoma | ATCC CCL 1600 |
| C127I | Mouse Fibroblast | ATCC CCL 1616 |
| 293 | Human Embyronal Kidney | ATCC CRL 1573 |
| HS-Sultan | Human Plasma Cell Plasmocytoma | ATCC CCL 1484 |
| BHK-21 | Baby Hamster Kidney | ATCC CCL 10 |

A preferred eukaryotic cell line of use in expresing the fusion proteins of this invention is the widely available cell line AV12-664 (hereinafter "AV12"). This cell line is available from the American Type Culture Collection under the accession number ATCC CRL 9595. The AV12 cell line was constructed by injecting a Syrian hamster in the scruff of the neck with human adenovirus 12 and isolating cells from the resulting tumor.

A wide variety of vectors, some of which are discussed below, exists for the transformation of such mammalian host cells, but the specific vectors described herein are in no way intended to limit the scope of the present invention. The sequences encoding the proteins of the invention are easily removed from the deposited strains by selection of the appropriate restriction endonucleases and inserted in any of the vectors described herein through routine purification, ligation and transfection techniques.

The pSV2-type vectors comprise segments of the simian virus 40 (SV40) genome that constitute a defined eukaryotic transcription unit-promoter, intervening sequence, and polyadenylation site. In the absence of the SV40 T antigen, the plasmid pSV2-type vectors transform mammalian and other eukaryotic host cells by integrating into the host cell chromosomal DNA. A large number of plasmid pSV2-type vectors have been constructed, such as plasmid pSV2-gpt, pSV2-neo, pSV2-dhfr, pSV2-hyg, and pSV2-b-globin, in which the SV40 promoter drives transcription of an inserted gene. These vectors are suitable for use with the coding sequences of the present invention and are widely available from sources such as the ATCC or the Northern Regional Research Laboratory (NRRL), 1815 N. University Street, Peoria, Ill., 61604.

The plasmid pSV2-dhfr (ATCC 37146) comprises a murine dihydrofolate reductase (dhfr) gene under the control of the SV40 early promoter. Under the appropriate conditions, the dhfr gene is known to be amplified, or copied, in the host chromosome. This amplification can result in the amplification of closely-associated DNA sequences and can, therefore, be used to increase production of a protein of interest. See. e.g., J. Schimke, *Cell*, 35:705–713 (1984).

Plasmids constructed for expression of the proteins of the present invention in mammalian and other eukaryotic host cells can utilize a wide variety of promoters. The present invention is in no way limited to the use of the particular promoters exemplified herein. Promoters such as the SV40 late promoter, promoters from eukaryotic genes, such as, for example, the estrogen-inducible chicken ovalbumin gene, the interferon genes, the gluco-corticoid-inducible tyrosine aminotransferase gene, and the thymidine kinase gene, and the major early and late adenovirus genes can be readily isolated and modified to express the genes of the present invention. Eukaryotic promoters can also be used in tandem to drive expression of a coding sequence of this invention. Furthermore, a large number of retroviruses are known that infect a wide range of eukaryotic host cells. The long terminal repeats in the retroviral DNA frequently encode functional promoters and, therefore, may be used to drive expression of the nucleic acids of the present invention.

Plasmid pRSVcat (ATCC 37152) comprises portions of a long terminal repeat of the Rous Sarcoma virus, a virus known to infect chickens and other host cells. This long terminal repeat contains a promoter which is suitable for use in the vectors of this invention. H. Gorman, et al., *Proceedinas of the National Academy of Sciences (USA)*, 79:6777 (1982). The plasmid pMSVi (NRRL B-15929) comprises the long terminal repeats of the Murine Sarcoma virus, a virus known to infect mouse and other host cells. The mouse metallothionein promoter has also been well characterized for use in eukaryotic host cells and is suitable for use in the expression of the nucleic acids of the present invention. The mouse metallothionein promoter is present in the plasmid pdBPV-MMTneo (ATCC 37224) which can serve as the starting material of other plasmids of the present invention.

A useful expression vector system employs one of a series of vectors containing the BK enhancer, an enhancer derived from the BK virus, a human papovavirus. The most preferred such vector systems are those which employ not only the BK enhancer but also the adenovirus-2-early region 1A (E1A) gene product. The E1A gene product (actually, the E1A gene produces two products, which are collectively referred to herein as "the E1A gene product") is an immediate-early gene product of adenovirus, a large DNA virus.

A eucaryotic expression vector that can be employed in the present invention is the phd series of vectors which comprise a BK enhancer in tandem with the adenovirus late promoter to drive expression of useful products in eukaryotic host cells. The construction and method of using the phd plasmid, as well as related plasmids, are described in U.S. Pat. No. 5,242,688, issued Sep. 7, 1993, and U.S. Pat. No. 4,992,373, issued Feb. 12, 1991, each of which are incorporated herein by reference. *Escherichia coli* K12 GM48 cells harboring the plasmid phd are available as part of the permanent stock collection of the Northern Regional Research Laboratory under accession number NRRL B-18525. The plasmid may be isolated from this culture using standard techniques.

The plasmid phd contains a unique BclII site which may be utilized for the insertion of the gene encoding the protein of interest. The skilled artisan understands that linkers or adapters may be employed in cloning the gene of interest into this BclI site. The phd series of plasmids functions most efficiently when introduced into a host cell which produces the E1A gene product, cell lines such as AV12-664, 293 cells, and others, described supra.

Transformation of the mammalian cells can be performed by any of the known processes including, but not limited to, the protoplast fusion method, the calcium phosphate co-precipitation method, electroporation and the like. See. e.g., J. Sambrook, et al., supra, at 3:16.30–3:16.66.

In addition to prokaryotes and mammalian host cells, eukaryotic microbes such as yeast cultures may also be used. The imperfect fungus *Saccharomyces cerevisiae*, or common baker's yeast, is the most commonly used eukaryotic microorganism, although a number of other strains are commonly available. For expression in Saccharomyces sp., the plasmid YRp7 (ATCC-40053), for example, is commonly used. See. e.g., L. Stinchcomb, et al., *Nature* (London), 282:39 (1979); J. Kingsman et al., *Gene*, 7:141 (1979); S. Tschemper et al., *Gene*, 10:157 (1980). This plasmid already contains the trp gene which provides a selectable marker for a mutant strain of yeast lacking the ability to grow in tryptophan.

Suitable promoting sequences for use with yeast hosts include the promoters for 3-phosphoglycerate kinase [found on plasmid pAP12BD (ATCC 53231) and described in U.S. Pat. No. 4,935,350, issued Jun. 19, 1990, incorporated herein by reference] or other glycolytic enzymes such as enolase [found on plasmid PAC1 (ATCC 39532)], glyceraldehyde-3-phosphate dehydrogenase [derived from plasmid pHcGAPC1 (ATCC 57090, 57091)], hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase, as well as the alcohol dehydrogenase and pyruvate decarboxylase genes of *Zymomonas mobilis* (U.S. Pat. No. 5,000,000 issued Mar. 19, 1991, incorporated herein by reference).

Other yeast promoters, which are inducible promoters, having the additional advantage of their transcription being controllable by varying growth conditions, are the promoter regions for alcohol dehydrogenase 2, isocytochrome C, acid phosphatase, degradative enzymes associated with nitrogen metabolism, metallothionein [contained on plasmid vector pCL28XhoLHBPV (ATCC 39475) and described in U.S. Pat. No. 4,840,896, incorporated herein by reference], glyceraldehyde 3-phosphate dehydrogenase, and enzymes responsible for maltose and galactose [e.g. GAL1 found on plasmid pRY121 (ATCC 37658)] utilization. Suitable vectors and promoters for use in yeast expression are further described in R. Hitzeman et al., European Patent Publication No. 73,657A. Yeast enhancers such as the UAS Gal from *Saccharomyces cerevisiae* (found in conjuction with the CYC1 promoter on plasmid YEpsec—hI1beta ATCC 67024), also are advantageously used with yeast promoters.

Other routes of production are well known to skilled artisans. In addition to the plasmids discussed above, it is well known in the art that some viruses are also appropriate vectors. For example, the adenovirus, the adeno-associated virus, the vaccinia virus, the herpes virus, the baculovirus, and the rous sarcoma virus are useful. Such a method is described in U.S. Pat. No. 4,775,624, incorporated herein by reference. Several alternate methods of expression are described in J. Sambrook, et al., supra, at 16.3–17.44.

In addition to cloning and expressing the genes of interest in the systems discussed above, the proteins of the present invention may also be produced using a variety of other organisms, including, for example, Spodoptera (Sf9 as host for baculovirus), and Saccharomyces. The more preferred cell line for use in the present invention is Sf9.

The preferred expression systems for use in the present invention are the various Baculovirus systems. One such expression system is the pFastBac1 expression system, which is commercially available from the Life Technologies group of Gibco BRL Products as Catalog No. 10360-016. Life Technologies, P.O. Box 68, Grand Island, N.Y. 14072, Telephone: 800 828 6686. pFastBac1 which was derivatized by adding a GST (glutathione-S-transferase) sequence from pGEX-2 (commercially available from Pharmacia Biotech, Inc., Piscataway, N.J., Catalog #27-4801-01, GeneBank Accession #U13850) was also used. Another expression system, the Bac-To-Bac Baculovirus Expression System, is available from Life Technologies (Catalog No. 10359-016).

In addition, another vector used in the present invention, pVL1393 (commercially available from Invirogen Corp., San Diego, Calif., Catalog #V1392-20) was derivatized by adding a GST (glutathione-S-transferase) sequence from pGEX-2 (commercially available from Pharmacia Biotech, Inc., Piscataway, N.J., Catalog #27-4801-01, GeneBank Accession #U13850).

These derivitized vectors were used in the construction of plasmids encoding various BRCA-1 fragments. These plasmids direct the synthesis of proteins which are fused at their amino termini with GST. The GST "handle" facilitated purification of the BRCA-1 fragments using a general procedure which has been described in the current literature. The Sf9 cells used are also commercially available.

Baculovirus expression systems are well known in the art and numerous scientific articles and "methods" books are available on the subject. The Life Technologies technical literature provides excellent guidance for producing products of interest via Baculovirus expression. The preferred techniques for Baculovirus expression of the sequences of the present invention are those provided in the product literature. Minor variations such as linker construciton and the like are considered in light of the advanced state of this art as too trivial to warrant discussion. In the event skilled artisans elect to depart from the commercially available Baculovirus systems, the present inventors recommend *Baculovirus Expression Vectors-A Laboratory Manual*, O'Reilly, David R., Miller, Lois K., and Luckow, Verne A., W. H. Freeman and Company, New York, N.Y. as a source of additional information on any protocol required for successful expression of polypeptides in Baculovirus systems.

Skilled artisans also recognize that some alterations of the amino acids will fail to change the function of the amino acid compound. For instance, some hydrophobic amino acids may be exchanged for other hydrophobic amino acids. Those altered amino acid compounds which confer substantially the same function in substantially the same manner as the exemplified amino acid compound are also encompassed within the present invention. Typical such conservative substitutions attempt to preserve the: (a) secondary or tertiary structure of the polypeptide backbone; (b) the charge or hydrophobicity of the residue; or (c) the bulk of the side chain. Some examples of such conservative substitutions of amino acids, resulting in the production of proteins which are functional equivalents of the protein kinases of the present invention are shown in Table II, infra.

TABLE II

| Original Residue | Exemplary Substitutions |
| --- | --- |
| Ala | Ser, Gly |
| Arg | Lys |
| Asn | Gln, His |
| Asp | Glu |
| Cys | Ser |
| Gln | Asn |
| Glu | Asp |
| Gly | Pro, Ala |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

These substitutions may be introduced into the protein in a variety of ways, such as during the chemical synthesis or by chemical modification of an amino acid side chain after the protein has been prepared.

Alterations of the protein may also be induced by alterations of the nucleic acid compounds which encode these proteins. These mutations of the nucleic acid compound may be generated by either random mutagenesis techniques, such as those techniques employing chemical mutagens, or by site-specific mutagenesis employing oligonucleotides. Those nucleic acid compounds which confer substantially the same function in substantially the same manner as the exemplified nucleic acid compounds are also encompassed within the present invention.

As skilled artisans will recognize, the amino acid compounds of the present invention can be encoded by a multitude of different nucleic acid sequences because most of the amino acids are encoded by more than one nucleic acid triplet due to the degeneracy of the amino acid code. Because these alternative nucleic acid sequences would encode the same amino acid sequences, the present invention further comprises these alternate nucleic acid sequences.

The genes encoding the DNA molecules of the present invention may be produced using synthetic methodology. This synthesis of nucleic acids is well known in the art. See, e.g., E. L. Brown, R. Belagaje, M. J. Ryan, and H. G. Khorana, *Methods in Enzymology*, 68:109–151 (1979). The DNA segments corresponding to the proteins are generated using conventional DNA synthesizing apparatus such as the Applied Biosystems Model 380A or 380B DNA synthesizers (commercially available from Applied Biosystems, Inc., 850 Lincoln Center Drive, Foster City, Calif. 94404) which employ phosphoramidite chemistry. In the alternative, the more traditional phosphotriester chemistry may be employed to synthesize the nucleic acids of this invention. See. e.g., M. J. Gait, ed., OLIGONUCLEOTIDE SYNTHESIS, A PRACTICAL APPROACH, (1984).

DNA sequences of the present invention may be designed to possess restriction endonuclease cleavage sites at either end of the transcript to facilitate isolation from and integration into expression and amplification plasmids. The choice of restriction sites are chosen so as to properly orient the coding sequence with control sequences to achieve proper in-frame reading and expression of the molecule. A variety of other such cleavage sites may be incorporated depending on the particular plasmid constructs employed and may be generated by techniques well known in the art.

In an alternative methodology, the coding regions of the desired DNA sequences can be generated using the polymerase chain reaction as described in U.S. Pat. No. 4,889,818, which is incorporated herein by reference.

The examples of the present invention provide sources for reagents, however it will be understood that numerous vendors market reagents of high quality for use in the protocols and procedures described below and the substitution of reagents or protocols is contemplated by the present invention and embraced in the scope thereof. All temperatures unless otherwise noted are expressed in degrees Centigrade. All percentages are on a weight per weight basis unless otherwise noted.

Skilled artisans wishing to practice the recombinant DNA aspects of the present invention are directed to the NIH guidelines for information on research involving recombinant DNA molecules. A copy of the current guidelines can be obtained from Office of Recombinant DNA Activities, National Institutes of Health, Building 31, Room 4B11, Bethesda, Md. 20892. Compliance with all such current regulations regarding vector selection, expression of human and animal genes and containment requirements is reguired by law.

The present invention also provides a method of diagnosing cancer and determining cancer prognosis. The method includes removing a tissue or cell sample from a subject suspected of having cancer and determining the level or activity of BRCA-1 related kinase in said sample, wherein a change in the level or activity of the BRCA-1 protein kinase compared to a normal sample indicates the presence of a cancer or indicates the level of malignancy of a cancer and, therefore, the most appropriate course of treatment.

As stated previously, the protein kinase of the present invention can be involved in signal transduction events that regulate important cellular processes. Other kinases have been identified previously for other tumor suppressor genes and oncogenes. And these kinases have provided important leads for cancer drug development. Such processes include, for example, cell differentiation and proliferation. Abnormal regulation or expression of the signal transduction machinery can lead to aberrant and malignant growth of the abnormally regulated cells. Abnormal expression might be associated with breast and or ovarian cancer. In addition, abnormal expression may also lead to the development of other types of cancers.

The important role that the protein kinase of the present invention plays in cellular processes can be advantageously used to diagnose early stages of cancer within a cell sample or tissue. A change in the amount or activity of such a protein kinase in a suspected sample, compared to a normal sample, can be indicative of cancerous stages and of their level of malignancy. Depending on whether the normal state is caused by the presence or absence of the kinase, the change can involve either an increase or decrease in the amount or activity of the kinase. One skilled in the art can measure these parameters and compare them to those obtained from a normal sample. Methods for determining the levels or activity of the kinase are known to one skilled in the art and include, for example, RNA and protein blot analysis, ELISA using specific antibodies to the protein kinase and direct measurement of catalytic activity such as kinase activity. Such methods can be found in Harlow et al, Antibodies: A Laboratory Manual, Cold Spring Harbor Laboratory (1989), which is incorporated herein by reference.

In the present invention, by using baculovirus as a vector, BRCA-1 and various fragments of BRCA-1 have been expressed as GST-fusion proteins in Sf9 cells. These proteins have in turn been used to isolate proteins that interact with BRCA-1.

These proteins were expressed as GST fusion proteins were partially purified in a single step using gluthathione-Sepharose. A control which did not include GST was included to ensure that GST was not the substrate.

In experiments searching for kinase activity, it was found that a region encoding a domain from exon 11 (amino acids 329–629) or a more C-terminal domain (B29, amino acids 1345–1653) of BRCA-1 was phosphorylated when incubated in the presence of $\gamma$-$^{32}$P-ATP. The activity was observed in the absence of the addition of an exogenous kinase. This kinase activity is lost upon washing the BRCA-1 region domain with 0.1% SDS but can be restored when incubated with NP-40 lysates prepared from Sf9 cells or from lysates prepared from breast or ovarian cell lines. Analysis of other regions of BRCA-1 indicate that the kinase activity is specific for the domain from exon 11 or C-terminal region of BRCA-1 since GST fusion proteins from other regions do not incorporate phosphate following addition of ATP. This data indicates the potential for in-vivo modulation of BRCA-1 by phosphorylation. In support of this, $^{32}$P-labeled BRCA-1 was immunoprecipitated from cells which were metabolically labeled with $^{32}$P-orthophosphate.

The ability of BRCA-1 protein kinase to mediate the phosphorylation of BRCA-1 protein is essential in the development of a multitude of indications. In developing agents which act to prevent/inhibit or promote the phosphorylation of the BRCA-1 protein, it would be desirable, therefore, to determine those agents which activate or inactivate and/or increase or decrease expression of BRCA-1 protein kinase. Generally, such assays include:

a) direct inhibition/direct activation assays which directly bind the protein kinase;

b) indirect inhibition/indirect activation assays which enhance or limit the activity of any associated factors involved in the phosphorylation of BRCA-1; and c) agents which increase or decrease the level of expression either through transcription or post-transcriptional events.

Preferably, the physically detectable means include assays in which binding of a labelled or tagged ligand is measured. Such assays are readily known to those skilled in the art such as scintillation proximity assays, radioimmuno assays, etc.

The instant invention provides such a screening system useful for discovering agents which prevent/inhibit or promote the phosphorylation of BRCA-1 protein, said screening system comprising the steps of:

a) isolating BRCA-1 protein kinase;

b) exposing said BRCA-1 protein kinase to a potential inhibitor and/or activator or surrogate of phosphorylation of BRCA-1 protein;

c) introducing BRCA-1 protein;

d) removing non-specifically bound molecules; and e) quantifying the concentration of bound potential inhibitor and/or activator and/or overall amount of phosphorylation induced by the BRCA-1 protein kinase.

This allows one to rapidly screen for compounds which prevent/inhibit or promote the phosphorylation of BRCA-1 proteins. Utilization of the screening system described above provides a sensitive and rapid means to determine compounds which prevent/inhibit phosphorylation. This screening system may also be adapted to automated procedures such as a PANDEX® (Baxter-Dade Diagnostics) system allowing for efficient high-volume screening of potential therapeutic agents.

In such a screening protocol the BRCA-1 protein kinase, as described hereinbefore, can be prepared using recombinant DNA technology. A sample of a test compound is then introduced to the reaction vessel containing the BRCA-1 protein kinase followed by the addition of the BRCA-1 protein. In the alternative, the BRCA-1 protein may be added simultaneously with the test compound. The BRCA-1 protein kinase can then be inspected to determine the degree of binding exhibited.

For example, in a preferred method of the invention, radioactively or chemically labeled test compound may be used. As would be understood by the skilled artisan, these assays are performed such that the practitioner measures the radioactivity or fluorescence remaining with the protein kinase, not in the eluent. The eluent is then scored for the chemical label or radioactivity. The absence or diminution of the chemical label or radioactivity indicates the formation of the BRCA-1 protein kinase/compound complex. This indicates that the test compound has effectively formed a complex with the BRCA-1 protein kinase.

In the alternative, after the competition reaction has been performed the reaction mixture is then passed through a filter, the filter retaining the protein kinase and whatever is complexed with the protein kinase. The radioactivity on each filter is then measured in a scintillation counter. In such an assay higher amounts of radiolabel present indicate greater affinity for the receptor by the test compound.

The protein kinase may be free in solution or bound to a solid support. Whether the protein kinase is bound to a support or is free in solution, it is generally important that the conformation of the protein be conserved. In a preferred practice of the invention, therefore, the protein kinase is suspended in a hydrophobic environment employing natural or synthetic detergents, membrane suspensions, and the like. Preferred detergent complexes include, but are not limited to zwitterionic detergent 3-[(3-cholamidopropyl)-dimethylammonio]-1-propane sulfonate ("CHAPS") as well as sodium deoxycholate and various nonionic detergents.

Skilled artisans will recognize that desirable dissociation constant ($K_i$) values are dependent on the selectivity of the compound tested. For example, a compound with a $K_i$ which is less than 10 nM is generally considered an excellent candidate for drug therapy. However, a compound which has a lower affinity, but is selective for the particular receptor, may be an even better candidate. The present invention, however, provides radiolabeled competition assays, whether results therefrom indicate high affinity or low affinity to protein kinase, because skilled artisans will recognize that any information regarding binding or selectivity of a particular compound is beneficial in the pharmaceutical development of drugs.

A transcription-based screen can be used to ascertain the effect of a agent on gene expression. Since this type of screen measures activity from a transcriptional promoter, it will only assess a drug's ability to induce a change at the level of transcription. It does not measure effects that may occur post-transcriptionally. The assay relies on establishing a "reporter construct" which will mimic the expression characteristics of the gene of interest (the BRCA-1 protein kinase in the present case). The general reporter construct requires the use of the transcriptional promoter from the gene of interest since this is the region of the gene that controls its expression. This promoter region is cloned in front of (at the 5' end) a gene (called a reporter) whose activity is easily measured. The most common genes used as reporters include Chloramphenicol Acetyl Transferase (CAT), Luciferase, and β-Galactosidase. Each one of the genes produce proteins that have activities which can be measured accurately, and easily. In addition, the assays which have been developed are quite sensitive. The basic design of the assay involves transfecting the reporter construct (Promoter from gene of interest fused to the reporter gene) into a cell line (usually mammalian) and then treating the transfected cells with the agents to be tested. Agents which alter or modulate (decrease or increase) the expression from the construct relative to untreated controls (as measured by changes in either CAT, luciferase, β-galactosidase activity) are considered as potential lead compounds.

Preferably screens which measure the level of kinase activity (phosphorylation of BRCA-1) will be used.

The following examples are intended to further illustrate the present invention and are not to be interpreted as limiting the scope thereof. While the examples and detailed description sections of the present invention are sufficient to guide anyone of ordinary skill in the art in the practice of the present invention, skilled artisans are also directed to *Molecular Cloning A Laboratory Manual* Second Edition, Sambrook, J., Fritsch, E. F., and Maniatis, T., Cold Spring Harbor Press 1989 and *Current Protocols In Molecular Biology*, Ausubel, F. M., Brent, R., Kingston, R. E., Moore, D. D., Seidman, J. G., Smith, J. A., and Struhl, K. ,Ed. Greene Publishing Associates and Wiley-Interscience 1989. The aforementioned resources provide an excellent technical supplement to any discourse in genetic engineering.

EXAMPLES

Using baculoviral-based vectors, several segments of BRCA-1 were expressed as GST fusion proteins in Sf9 cells. The complete BRCA-1 protein was produced along with the following BRCA-1 fragments: B63 (SEQ ID NO:1) which encodes amino acid residues 329–629 of BRCA-1; B71 (SEQ ID NO:2) which encodes amino acid residues 329–435; B73 (SEQ ID NO:2) which encodes amino acids 329–435 (but not expressed as a GST fusion protein); B74 (SEQ ID NO:3) which encodes amino acid residues 329–525; B90 (SEQ ID NO:4) which encodes amino acid residues 329–421; B102 (SEQ ID NO:5) which encodes amino acid residues 379–408 and B29 (SEQ ID NO:6) which encodes amino acid residues 1365–1669; B72 (SEQ ID NO:8) which encodes amino acid residues 531–629 and B89 (SEQ ID NO:9) which encodes amino acid residues 433–525. All fragments of BRCA-1 were generated by PCR using the full length BRCA-1 cDNA as the template. The PCR fragments (with the exception of B73) were subsequently cloned into the baculovirus expression vectors containing a GST handle and were expressed using standard techniques known to those of ordinary skill in the art. B73 was cloned into a similar baculovirus expression vector which lacked the GST handle. The resulting proteins were used as reagents to identify proteins or activities which associate with or are a part of BRCA-1. Other regions of BRCA-1 were expressed but failed to show any associated kinase activity.

A KINASE ACTIVITY FROM INSECT CELLS CO-PURIFIES WITH BRCA-1

As noted, full-length BRCA-1 and the BRCA-1 fragments were expressed in Sf9 cells using a baculovirus based expression system. B63 was expressed as a fusion protein with glutathione-S-transferase (GST) whereas B73 was a later version of the same clone which was expressed without a GST handle. B45 was the clone which directs the synthesis of GST. Cells expressing B45, B63, B73 or full-length BRCA-1 were lysed by the addition of lysis buffer. These proteins were then captured from cell lysates using either Glutathione-Sepharose (B45 and B63) or Protein G agarose bound with BRCA-1 antibody (B73 and full-length BRCA-1). After washing three times with lysis buffer, proteins were incubated at 32° C. for 30 minutes in lysis buffer containing 1 $\mu$Ci/$\mu$L $\gamma$-$^{32}$P-ATP, 10 mM $MgCl_2$, 1 mM DTT. The resin-bound proteins were washed 2 times with lysis buffer, solubilized from the resin, and resolved on 8–16% polyacrylamide gradient gel. Phosphorylation of each protein was analyzed by autoradiography. The presence of a radiolabeled band of the appropriate molecular weight indicated phosphorylation. In these experiments, it was evident that B29, B63 and full length BRCA-1 all were phosphorylated indicating that these fragments were associated with a kinase activity.

The above experiments indicated that BRCA-1, particularly exon 11 and the B29 region, are associated with a kinase activity. The experiments described below were focused on defining further the regions of BRCA-1 which are important for this activity. In these experiments, truncated versions of B63 (namely, B71, B73, B74, B90, B89, B72 and B102) were expressed in Sf9 cells and purified on Glutathionine-Sepharose as described above. These fragments were assessed for their ability to act as kinase substrates by incubating them with γ-$^{32}$P-ATP. The results show that B71, B73, B74, B90 and B102 all are substrates indicating that at least one region of phosphorylation can be defined between amino acids 329–435.

| ANALYSIS OF BRCA-1 FRAGMENTS AS KINASE SUBSTRATES | | |
| --- | --- | --- |
| | | Kinase Substrate |
| B63 | (amino acids 329–629) | yes |
| B71 | (amino acids 329–435) | yes |
| B72 | (amino acids 531–629) | no |
| B73 | (amino acids 329–435) | yes |
| B74 | (amino acids 329–525) | yes |
| B89 | (amino acids 433–525) | no |
| B90 | (amino acids 329–421) | yes |
| B102 | (amino acids 379–408) | yes |

EVIDENCE FOR MULTIPLE SITES OF PHOSPHORYLATION

Results from the purification of B63 or its truncated derivative B71 (BRCA-1 amino acids 329–435) by HPLC suggested that multiple phosphorylation sites exist within the exon 11 region of BRCA-1. Specifically, the elution profile showed the presence of several closely migrating peaks that can be collapsed into a single pleak following treatment of the BRCA-1 peptides with alkaline phosphatase. One of these peaks corresponded to the phosphorylated derivative which resulted from incubating B71 with γ-$^{32}$P-ATP as described above. Biochemical studies which included purification and direct sequencing of tryptic peptides confirmed that multiple sites of phosphorylation exist between amino acids 329–435 with one specific site of phosphorylation being between amino acids 379–408.

BRCA-1 IS PHOSPHORYLATED IN HUMAN BREAST CELLS

MCF-7 or 184-A1 cells (human breast cell lines), grown on 60 mm culture dishes, were incubated with 1.0 mCi of $^{32}$P-orthophosphate for 4 hours. The cells were lysed by the addition of lysis buffer (25 mM HEPES, 150 mM NaCl, 0.5% NP-40, pH=7.5) and then immunopreciptated using monoclonal antibody specific to BRCA-1 (8F4.4) or a control antibody of the identical isotype (IgG1). Immune complexes were captured using Protein G agarose, solubilized and resolved on a 8–16% SDS-PAGE gradient gel. $^{32}$P-labeled proteins were analyzed by autoradiography. In vivo phosphorylation of BRCA-1 was confirmed by the presence of a radiolabelled band of the appropriate molecular weight (approximately 210 kDa). No such radiolabelled band appeared in IgG controls.

POTENTIAL PHOSPHORYLATION SITES WITHIN BRCA-1

Following the above experiments, computer analysis was done. Computer analysis predicted several potential sites of phosphorylation within the 5' End of Exon 11 (these have been underlined). Note that these sites are merely computer generated sites only and this does not imply that these are the only possible sites or are actual sites of phosphorylation within BRCA-1.

```
Asn Asp Arg Arg Thr Pro Ser Thr Glu Lys Lys Val Asp Leu Asn Ala
 1            5           10              15

Asp Pro Leu Cys Glu Arg Lys Glu Trp Asn Lys Gln Lys Leu Pro Cys
            20              25              30

Ser Glu Asn Pro Arg Asp Thr Glu Asp Val Pro Trp Ile Thr Leu Asn
        35              40              45

Ser Ser Ile Gln Lys Val Asn Glu Trp Phe Ser Arg Ser Asp Glu Leu
    50              55              60

Leu Gly Ser Asp Asp Ser His Asp Gly Glu Ser Glu Ser Asn Ala Lys
65              70              75              80

Val Ala Asp Val Leu Asp Val Leu Asn Glu Val Asp Glu Tyr Ser Gly
                85              90              95

Ser Ser Glu Lys Ile Asp Leu Leu Ala Ser Asp Pro His Glu Ala Leu
                100             105             110

Ile Cys Lys Ser Glu Arg Val His Ser Lys Ser Val Glu Ser Asn Ile
            115             120             125

Glu Asp Lys Ile Phe Gly Lys Thr Tyr Arg Lys Lys Ala Ser Leu Pro
    130             135             140

Asn Leu Ser His Val Thr Glu Asn Leu Ile Ile Gly Ala Phe Val Thr
145             150             155             160

Glu Pro Gln Ile Ile Gln Glu Arg Pro Leu Thr Asn Lys Leu Lys Arg
            165             170             175

Lys Arg Arg Pro Thr Ser Gly Leu His Pro Glu Asp Phe Ile Lys Lys
            180             185             190

Ala Asp Leu Ala Val Gln Lys Thr Pro Glu Met Ile Asn Gln Gly Thr
        195             200             205

Asn Gln Thr Glu Gln Asn Gly Gln Val Met Asn Ile Thr Asn Ser Gly
        210             215             220
```

-continued

```
His Glu Asn Lys Thr Lys Gly Asp Ser Ile Gln Asn Glu Lys Asn Pro
225              230                 235                 240

Asn Pro Ile Glu Ser Leu Glu Lys Glu Ser Ala Phe Lys Thr Lys Ala
            245                 250                 255

Glu Pro Ile Ser Ser Ser Ile Ser Asn Met Glu Leu Glu Leu Asn Ile
            260             265                 270

His Asn Ser Lys Ala Pro Lys Lys Asn Arg Leu Arg Arg Lys SerSer
        275             280                 285

Thr Arg His Ile His Ala Leu Glu Leu Val Val Ser Arg
    290                 295             300
```

Initial studies on phosphorylation concentrated on a small 5' fragment from BRCA-1 exon 11 (amino acids 329–629). Computer analysis indicated that this region, which we call B63, can be potentially phosphorylated by cAMP-dependent protein kinase (PKA), protein kinase C (PKC) and casein kinase II (CKII). No sites of tyrosine phosphorylation were identified by computer analysis.

KINASE ASSOCIATED WITH BRCA-1 FRAGMENT DOES NOT APPEAR TO BE PKA, PKC, OR CKII

B63 was prepared as described previously. The Sepharose bound fragment was then incubated with either lysate from Sf9 cells or with purified preparations of either PKA, PKC or CKII (each commercially available from Boehringer Mannheim). After a one hour incubation, the Sepharose-bound complexes were washed and then incubated with $\gamma^{32}$P-ATP as described previously. No phosphorylation of B63 was evident in samples that were incubated with either PKA or PKC and only minor phosphorylation was observed following incubation with CKII. Thus these data indicate that PKA, PKC or CKII are not the kinases responsible for phosphorylation of exon 11.

PHOSPHORYLATION ACTIVITY ASSOCIATED WITH BRCA-1 IS NOT DUE TO AUTOPHOSPHORYLATION

The results of the above experiments suggest that either BRCA-1 itself is a kinase capable of autophosphorylation, or that a kinase associates with BRCA-1 and remains bound during the purification process. Computer assisted sequence analysis does not support the first possibility since a search did not detect the precence of any hallmarks associated with known kinases. Thus, the phosphorylation detected was most likely due to a kinase which was physically bound to BRCA-1. The experiments outlined in A and B below support this hypothesis.

A. Phosphorylation activity was lost when BRCA-1 was washed with SDS. B63 produced as described above was bound to Glutathione-Sephrose in the absence or presence of SDS at concentrations from 0.05%–0.1% for 1 hour at 4° C. The Sepharose-bound proteins were then washed 4 times with lysis buffer and incubated with $\gamma$-$^{32}$P-ATP as described above. Phosphorylation of each protein was determined by SDS-PAGE followed by autoradiography.

B. Addition experiments showed that the activity of protein kinase could be separated from BRCA-1 if resin-bound (i.e., BRCA-1 bound to glutathione agarose) BRCA-1 was washed with 0.1% sodium dodecyl sulfate (SDS). Notably, kinase activity could be restored to the SDS washed BRCA-1 when the BRCA-1 fragment was incubated with lysates prepared from either Sf9 cells (insect cells) or from the human breast or ovarian cell lines. Pre-treatment of lysates from insect cells with SDS prior to mixing with BRCA-1 destroyed kinase activity, again suggesting that the kinase activity was a separate entity from BRCA-1. These data also indicate that the protein kinase is expressed in human derived cell lines. Another region of BRCA-1 that has potential as a region that either autophosphorylates or associates with a kinase, namely a region between amino acid residues 1365 and 1669 (B29) has been found.

```
SEQUENCES

SEQ ID NO:1 (B63)
Asn Asp Arg Arg Thr Pro Ser Thr Glu Lys Lys Val Asp Leu Asn Ala
1               5                   10                  15

Asp Pro Leu Cys Glu Arg Lys Glu Trp Asn Lys Gln Lys Leu Pro Cys
            20                  25                  30

Ser Glu Asn Pro Arg Asp Thr Glu Asp Val Pro Trp Ile Thr Leu Asn
        35                  40                  45

Ser Ser Ile Gln Lys Val Asn Glu Trp Phe Ser Arg Ser Asp Glu Leu
    50                  55                  60

Leu Gly Ser Asp Asp Ser His Asp Gly Glu Ser Glu Ser Asn Ala Lys
65                  70                  75                  80

Val Ala Asp Val Leu Asp Val Leu Asn Glu Val Asp Glu Tyr Ser Gly
                85                  90                  95

Ser Ser Glu Lys Ile Asp Leu Leu Ala Ser Asp Pro His Glu Ala Leu
            100                 105                 110
```

-continued

SEQUENCES

Ile Cys Lys Ser Glu Arg Val His Ser Lys Ser Val Glu Ser Asn Ile
            115                 120                 125

Glu Asp Lys Ile Phe Gly Lys Thr Tyr Arg Lys Lys Ala Ser Leu Pro
130                 135                 140

Asn Leu Ser His Val Thr Glu Asn Leu Ile Ile Gly Ala Phe Val Thr
145                 150                 155                 160

Glu Pro Gln Ile Ile Gln Glu Arg Pro Leu Thr Asn Lys Leu Lys Arg
                165                 170                 175

Lys Arg Arg Pro Thr Ser Gly Leu His Pro Glu Asp Phe Ile Lys Lys
                180                 185                 190

Ala Asp Leu Ala Val Gln Lys Thr Pro Glu Met Ile Asn Gln Gly Thr
            195                 200                 205

Asn Gln Thr Glu Gln Asn Gly Gln Val Met Asn Ile Thr Asn Ser Gly
210                 215                 220

His Glu Asn Lys Thr Lys Gly Asp Ser Ile Gln Asn Glu Lys Asn Pro
225                 230                 235                 240

Asn Pro Ile Glu Ser Leu Glu Lys Glu Ser Ala Phe Lys Thr Lys Ala
                245                 250                 255

Glu Pro Ile Ser Ser Ser Ile Ser Asn Met Glu Leu Glu Leu Asn Ile
                260                 265                 270

His Asn Ser Lys Ala Pro Lys Lys Asn Arg Leu Arg Arg Lys Ser Ser
            275                 280                 285

Thr Arg His Ile His Ala Leu Glu Leu Val Val Ser Arg
290                 295                 300

SEQ ID NO:2 (B71)

Asn Asp Arg Arg Thr Pro Ser Thr Glu Lys Lys Val Asp Leu Asn Ala
1               5                   10                  15

Asp Pro Leu Cys Glu Arg Lys Glu Trp Asn Lys Gln Lys Leu Pro Cys
                20                  25                  30

Ser Glu Asn Pro Arg Asp Thr Glu Asp Val Pro Trp Ile Thr Leu Asn
            35                  40                  45

Ser Ser Ile Gln Lys Val Asn Glu Trp Phe Ser Arg Ser Asp Glu Leu
    50                  55                  60

Leu Gly Ser Asp Asp Ser His Asp Gly Glu Ser Glu Ser Asn Ala Lys
65                  70                  75                  80

Val Ala Asp Val Leu Asp Val Leu Asn Glu Val Asp Glu Tyr Ser Gly
                85                  90                  95

Ser Ser Glu Lys Ile Asp Leu Leu Ala Ser
            100                 105

SEQ ID NQ:3 (B74)

Asn Asp Arg Arg Thr Pro Ser Thr Glu Lys Lys Val Asp Leu Asn Ala
1               5                   10                  15

Asp Pro Leu Cys Glu Arg Lys Glu Trp Asn Lys Gln Lys Leu Pro Cys
                20                  25                  30

Ser Glu Asn Pro Arg Asp Thr Glu Asp Val Pro Trp Ile Thr Leu Asn
            35                  40                  45

Ser Ser Ile Gln Lys Val Asn Glu Trp Phe Ser Arg Ser Asp Glu Leu
    50                  55                  60

Leu Gly Ser Asp Asp Ser His Asp Gly Glu Ser Glu Ser Asn Ala Lys
65                  70                  75                  80

Val Ala Asp Val Leu Asp Val Leu Asn Glu Val Asp Glu Tyr Ser Gly

-continued

SEQUENCES

```
                    85                  90                  95
Ser Ser Glu Lys Ile Asp Leu Leu Ala Ser Asp Pro His Glu Ala Leu
                    100                 105                 110

Ile Cys Lys Ser Glu Arg Val His Ser Lys Ser Val Glu Ser Asn Ile
                    115                 120                 125

Glu Asp Lys Ile Phe Gly Lys Thr Tyr Arg Lys Ala Ser Leu Pro
    130                 135                 140

Asn Leu Ser His Val Thr Glu Asn Leu Ile Ile Gly Ala Phe Val Thr
145                 150                 155                 160

Glu Pro Gln Ile Ile Gln Glu Arg Pro Leu Thr Asn Lys Leu Lys Arg
                    165                 170                 175

Lys Arg Arg Pro Thr Ser Gly Leu His Pro Glu Asp Phe Ile Lys Lys
                    180                 185                 190

Ala Asp Leu Ala
            195
```

SEQ ID NO:4 (B90)

```
Asn Asp Arg Arg Thr Pro Ser Thr Glu Lys Lys Val Asp Leu Asn Ala
1                   5                   10                  15

Asp Pro Leu Cys Glu Arg Lys Glu Trp Asn Lys Gln Lys Leu Pro Cys
                    20                  25                  30

Ser Glu Asn Pro Arg Asp Thr Glu Asp Val Pro Trp Ile Thr Leu Asn
                    35                  40                  45

Ser Ser Ile Gln Lys Val Asn Glu Trp Phe Ser Arg Ser Asp Glu Leu
                    50                  55                  60

Leu Gly Ser Asp Asp Ser His Asp Gly Glu Ser Glu Ser Asn Ala Lys
65                  70                  75                  80

Val Ala Asp Val Leu Asp Val Leu Asn Glu Val Asp
                    85                  90
```

SEQ ID NO:5 (B102)

```
Ile Gln Lys Val Asn Glu Trp Phe Ser Arg Ser Asp Glu Leu Leu Gly
1                   5                   10                  15

Ser Asp Asp Ser His Asp Gly Glu Ser Glu Ser Asn Ala Lys
                    20                  25                  30
```

SEQ ID NO:6 (B29)

```
Glu Glu Arg Gly Thr Gly Leu Glu Glu Asn Asn Gln Glu Glu Gln Ser
1                   5                   10                  15

Met Asp Ser Asn Leu Gly Glu Ala Ala Ser Gly Cys Glu Ser Glu Thr
                    20                  25                  30

Ser Val Ser Glu Asp Cys Ser Gly Leu Ser Ser Gln Ser Asp Ile Leu
                    35                  40                  45

Thr Thr Gln Gln Arg Asp Thr Met Gln His Asn Leu Ile Lys Leu Gln
                    50                  55                  60

Gln Glu Met Ala Glu Leu Glu Ala Val Leu Glu Gln His Gly Ser Gln
65                  70                  75                  80

Pro Ser Asn Ser Tyr Pro Ser Ile Ile Ser Asp Ser Ser Ala Leu Glu
                    85                  90                  95

Asp Leu Arg Asn Pro Glu Gln Ser Thr Ser Glu Lys Ala Val Leu Thr
                    100                 105                 110

Ser Gln Lys Ser Ser Glu Tyr Pro Ile Ser Gln Asn Pro Glu Gly Leu
                    115                 120                 125

Ser Ala Asp Lys Phe Glu Val Ser Ala Asp Ser Ser Thr Ser Lys Asn
```

SEQUENCES

```
                130                 135                 140
Lys Glu Pro Gly Val Glu Arg Ser Ser Pro Ser Lys Cys Pro Ser Leu
145                 150                 155                 160

Asp Asp Arg Trp Tyr Met His Ser Cys Ser Gly Ser Leu Gln Asn Arg
                165                 170                 175

Asn Tyr Pro Ser Gln Glu Glu Leu Ile Lys Val Val Asp Val Glu Glu
                180                 185                 190

Gln Gln Leu Glu Glu Ser Gly Pro His Asp Leu Thr Glu Thr Ser Tyr
                195                 200                 205

Leu Pro Arg Gln Asp Leu Glu Gly Thr Pro Tyr Leu Glu Ser Gly Ile
                210                 215                 220

Ser Leu Phe Ser Asp Asp Pro Glu Ser Asp Pro Ser Glu Asp Arg Ala
225                 230                 235                 240

Pro Glu Ser Ala Arg Val Gly Asn Ile Pro Ser Ser Thr Ser Ala Leu
                245                 250                 255

Lys Val Pro Gln Leu Lys Val Ala Glu Ser Ala Gln Ser Pro Ala Ala
                260                 265                 270

Ala His Thr Thr Asp Thr Ala Gly Tyr Asn Ala Met Glu Glu Ser Val
                275                 280                 285

Ser Arg Glu Lys Pro Glu Leu Thr Ala Ser Thr Glu Arg Val Asn Lys
                290                 295                 300
Arg Met Ser Met Val
305

SEQ ID NQ:7 (B73)
Asn Asp Arg Arg Thr Pro Ser Thr Glu Lys Lys Val Asp Leu Asn Ala
1                   5                   10                  15

Asp Pro Leu Cys Glu Arg Lys Glu Trp Asn Lys Gln Lys Leu Pro Cys
                20                  25                  30

Ser Glu Asn Pro Arg Asp Thr Glu Asp Val Pro Trp Ile Thr Leu Asn
                35                  40                  45

Ser Ser Ile Gln Lys Val Asn Glu Trp Phe Ser Arg Ser Asp Glu Leu
                50                  55                  60

Leu Gly Ser Asp Asp Ser His Asp Gly Glu Ser Glu Ser Asn Ala Lys
65                  70                  75                  80

Val Ala Asp Val Leu Asp Val Leu Asn Glu Val Asp Glu Tyr Ser Gly
                85                  90                  95

Ser Ser Glu Lys Ile Asp Leu Leu Ala Ser
                100                 105

SEQ ID NQ:8 (B72)

Met Ile Asn Gln Gly Thr Asn Gln Thr Glu Gln Asn Gly Gln Val Met
1                   5                   10                  15

Asn Ile Thr Asn Ser Gly His Glu Asn Lys Thr Lys Gly Asp Ser Ile
                20                  25                  30

Gln Asn Glu Lys Asn Pro Asn Pro Ile Glu Ser Leu Glu Lys Glu Ser
                35                  40                  45

Ala Phe Lys Thr Lys Ala Glu Pro Ile Ser Ser Ile Ser Asn Met
                50                  55                  60

Glu Leu Glu Leu Asn Ile His Asn Ser Lys Ala Pro Lys Lys Asn Arg
65                  70                  75                  80

Leu Arg Arg Lys Ser Ser Thr Arg His Ile His Ala Leu Glu Leu Val
                85                  90                  95

Val Ser Arg
```

| SEQUENCES |
| --- |
| SEQ ID NO:9 (B89) |
| Ala Ser Asp Pro His Glu Ala Leu Ile Cys Lys Ser Glu Arg Val His<br>1               5                   10                  15 |
| Ser Lys Ser Val Glu Ser Asn Ile Glu Asp Lys Ile Phe Gly Lys Thr<br>            20                  25                  30 |
| Tyr Arg Lys Lys Ala Ser Leu Pro Asn Leu Ser His Val Thr Glu Asn<br>        35                  40                  45 |
| Leu Ile Ile Gly Ala Phe Val Thr Glu Pro Gln Ile Ile Gln Glu Arg<br>    50                  55                  60 |
| Pro Leu Thr Asn Lys Leu Lys Arg Lys Arg Pro Thr Ser Gly Leu<br>65                  70                  75                  80 |
| His Pro Glu Asp Phe Ile Lys Lys Ala Asp Leu Ala Val<br>                85                  90 |

What is claimed is:

1. A substantially purified protein kinase which catalyzes the phosphorylation of amino acid residues of BRCA-1 protein regions having sequences given by SEQ ID NOS: 1 and 6.

2. The protein kinase of claim 1 wherein the pI of the protein kinase is from about 5.0 to 8.0.

3. The protein kinase of claim 1 wherein either $Mg^{2+}$ or $Mn^{2+}$ is required but $Ca^{2+}$ is not required for the protein kinase to be active.

4. The protein kinase of claim 1 wherein the amino acid residues of BRCA-1 protein have a sequence given by SEQ ID NO:2.

5. The protein kinase of claim 1 wherein the amino acid residues of BRCA-1 protein have a sequence given by SEQ ID NO:3.

6. The protein kinase of claim 1 wherein the amino acid residues of BRCA-1 protein have a sequence given by SEQ ID NO:4.

7. The protein kinase of claim 1 wherein the amino acid residues of BRCA-1 protein have a sequence given by SEQ ID NO:5.

* * * * *